(12) United States Patent
Gilis

(10) Patent No.: US 6,303,147 B1
(45) Date of Patent: Oct. 16, 2001

(54) BIOADHESIVE SOLID DOSAGE FORM

(75) Inventor: Paul Marie Victor Gilis, Beerse (BE)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 09/091,685

(22) PCT Filed: Dec. 20, 1996

(86) PCT No.: PCT/EP96/05884

§ 371 Date: Jun. 19, 1998

§ 102(e) Date: Jun. 19, 1998

(87) PCT Pub. No.: WO97/24109

PCT Pub. Date: Jul. 10, 1997

(30) Foreign Application Priority Data

Dec. 27, 1995 (EP) .................................................. 95203649

(51) Int. Cl.[7] .................................. A61K 9/02; A61K 9/20
(52) U.S. Cl. .......................... 424/484; 424/434; 424/436; 424/464; 424/465; 424/486; 424/488
(58) Field of Search ..................................... 424/465, 434, 424/436, 464, 484; 514/360, 680

(56) References Cited

U.S. PATENT DOCUMENTS

| 3,554,764 | | 1/1971 | Yoder ...................................... 99/101 |
| 5,330,761 | * | 7/1994 | Baichwal .............................. 424/469 |
| 5,370,878 | | 12/1994 | Shah ..................................... 424/469 |
| 5,656,283 | | 8/1997 | Brummer et al. .................... 424/433 |
| 5,662,933 | * | 9/1997 | Baichwal et al. .................... 424/457 |
| 5,759,580 | | 6/1998 | Jans et al. ............................ 424/489 |

FOREIGN PATENT DOCUMENTS

451433 * 10/1991 (EP) .

* cited by examiner

*Primary Examiner*—Thurman K. Page
*Assistant Examiner*—Alysia Berman
(74) *Attorney, Agent, or Firm*—Mary Appollina

(57) ABSTRACT

The present invention is concerned with bioadhesive pharmaceutical compositions comprising a pharmaceutically effective amount of an active ingredient, from 80% to 98.8% (w/w/) pre-gelatinized starch, and from 1% to 10% (w/w) of a hydrophilic matrix forming polymer, characterized in that the composition further comprises from 0.2% to 5% (w/w) alkali$C_{16-22}$alkyl fumarate as a lubricant; solid dosage forms such as tablets which are suitable for oral, nasal, rectal and vaginal administration; processes of preparing the compositions and solid dosage forms.

12 Claims, No Drawings

БИОАДHESIVE SOLID DOSAGE FORM

CROSS REFERENCE TO RELATED APPLICATIONS

This application is a National Stage application under 35 U.S.C. 371 of PCT/EP96/05884 filed Dec. 20, 1996, which claims priority from EP95.203.649.9, filed Dec. 27, 1995.

The present invention is concerned with bioadhesive compositions and solid dosage forms prepared therefrom which have a regular and prolonged release pattern for a locally acting ingredient or also for a systemically acting drug, and which are suitable for oral, nasal, rectal and vaginal administration.

Known bioadhesive solid dosage forms are described, for example, in GB-2,042,888 (Teijin). Those dosage forms comprise an active ingredient, 50 to 95% of a cellulose ether and 50 to 5% of a high molecular weight crosslinked polyacrylic acid (carboxyvinyl polymer, carbomer, carbopol). Commercially available bioadhesive dosage forms are often double-layered (multi-layered) preparations with one adhesive layer and at least one non-adhesive layer (e.g. Teijin's Aftach®, Triamcinolone Acetonide Plastering Tablet).

An improved bioadhesive solid dosage form comprising a mixture of 5% polyacrylic acid (Carbopol 934) with pregelatinized starch (drum-dried waxy maize) was described in EP-0,451,433 and in Eur. J. Clin. Pharmacol. (1992) 43: 137–140. Its main advantages were excellent bioadhesion and the total absence of tissue irritation. The development of a buccal tablet on an industrial scale using these disclosures proved unfeasible because of the impossibility to obtain industrially meaningful quantities of the lubricant sodium benzoate in micronized form (i.e. with a very high specific surface). All attempts to prepare buccal tablets with a non-micronized lubricant or without a lubricant failed. The lubricant proved to be essential in order to compress tablets from a granulate. Without it, the tablets stuck to the punches and dies used. A non-micronized lubricant then had the drawback that it needed to be used in unacceptably high amounts and that as a result thereof it affected such properties as bioavailability, release characteristics, taste and mouthfeel.

Consequently, a different lubricant having acceptable properties was called for. First, it was found that the two problems of taste and mouthfeel could be dealt with by restricting the lubricant used to a water-soluble lubricant. Poorly water-soluble lubricants such as magnesium stearate in combination with the bioadhesive carrier left a soap-like taste in the mouth. All of the problems could be solved satisfactorily by using a water-soluble alkali $C_{16-22}$alkyl fumarate as lubricant, in particular sodium stearyl fumarate. A surprising finding was that the lubricant did not cause any loss of bioadhesion and did not negatively affect the release characteristics of the tablet. Upon further upscaling of the wet granulation process used thus far for preparing tablets from the novel bioadhesive composition, yet another problem was encountered, namely disintegration of the granulate during its drying in e.g. a fluid bed drier. This problem has now been solved by dry compaction of some of the ingredients before compression.

The present invention relates to a bioadhesive pharmaceutical composition comprising a pharmaceutically effective amount of an active ingredient and from 80% to 98.8% (w/w) of a mixture of pre-gelatinized starch, from 1% to 10% (w/w) hydrophylic matrix forming polymer, characterized in that the composition further comprises from 0.2% to 5% (w/w) alkali $C_{6-22}$alkyl fumarate as a lubricant.

Amounts of lubricants below 0.2% cannot be considered effective, whereas their use in amounts in excess of 5% do not further improve the process of compression into tablets, but on the contrary tend to impart undesired properties on the formulations. An amount of about 2% is considered optimal. Preferably, said lubricant is sodium stearyl fumarate which is commercially available in micronized form (Pruv®) and in addition is water-soluble and practically tasteless.

The amount of hydrophilic matrix forming polymer in the bioadhesive compositions according to the present invention in general ranges from 2.5% to 7.5% (w/w), and most preferably is about 5% (w/w). Examples of hydrophilic matrix forming polymers are polyacrylic acid (carbomer), hydroxyethyl cellulose, hydroxypropyl cellulose, hydroxypropyl methylcellulose, sodium carboxymethyl cellulose, polyvinyl alcohol and mixtures thereof. Polyacrylic acid and in particular carbomer 974P is useful in ensuring that the dosage forms prepared from the bioadhesive compositions have a regular and prolonged release pattern of the active ingredient. Therefore it is the preferred hydrophilic matrix forming polymer in the bioadhesive compositions according to the present invention.

In order to prevent the abrasion of the granulate during the tablet compression, the composition according to the invention advantageously further comprises a glidant. An example of such a glidant is colloidal anhydrous silica. The amount of glidant can range from 0% to about 1% (w/w) and preferably is about 0.2%.

A preferred composition according to the present invention comprises by weight based on the total weight of the composition:

from 0.001% to 10% active ingredient;
from 80% to 98.8% pre-gelatinized starch;
from 1 to 10% hydrophilic matrix forming polymer;
from 0.2% to 5% sodium stearyl fumarate;
from 0% to 1% glidant.

Suitable active ingredients are those which exert a local physiological effect, as well as those which exert a systemic effect, either following penetrating the mucosa or—in the case of oral administration—following transport to the gastro-intestinal tract with saliva. The bioadhesive dosage forms prepared from the compositions according to the present invention are particularly suitable for active ingredients which exert their activity during an extended period of time. Examples thereof are: analgesic and anti-inflammatory drugs (NSAIDs, acetyl salicylic acid, diclofenac sodium, ibuprofen, indomethacin, ketoprofen, meclofenamate sodium, mefenamic acid, naproxen sodium, paracetamol, piroxicam, tolmetin sodium); anti-arrhythmic drugs (procainamide HCl, quinidine sulphate, verapamil HCl); antibacterial agents (amoxicillin, ampicillin, benzathine penicillin, benzylpenicillin, cefaclor, cefadroxil, cephalexin, chloramphenicol, ciprofloxacin, clavulanic acid, clindamycin HCl, doxyxycline HCl, erythromycin, flucloxacillin sodium, kanamycin sulphate, lincomycin HCl, minocycline HCl, nafcillin sodium, nalidixic acid, neomycin, norfloxacin, ofloxacin, oxacillin, phenoxymethyl-penicillin potassium); anti-coagulants (warfarin); antidepressants (amitriptyline HCl, amoxapine, butriptyline HCl, clomipramine HCl, desipramine HCl, dothiepin HCl, doxepin HCl, fluoxetine, gepirone, imipramine, lithium carbonate, mianserin HCl, milnacipran, nortriptyline HCl, paroxetine HCl); anti-diabetic drugs (glibenclamide); antifungal agents (amphotericin, clotrimazole, econazole, fluconazole, flucytosine, griseofulvin, itraconazole, ketoconazole, miconazole nitrate, nystatin); antihistamines (astemizole, cinnarizine, cyproheptadine HCl, flunarizine, oxatomide, promethazine, terfenadine); anti-hypertensive drugs (captopril, enalapril, ketanserin, lisinopril, minoxidil, prazosin HCl, ramipril, reserpine); anti-muscarinic agents (atropine sulphate, hyoscine); antivirals (acyclovir, AZT, ddC, ddI, ganciclovir, loviride, tivirapine, 3TC, delavirdine, indinavir, nelfinavir, ritonavir, saquinavir); sedating agents (alprazolam, buspirone HCl, chlordiazepoxide HCl, chlorpromazine, clozapine, diazepam, flupenthixol HCl, fluphenazine, flurazepam, lorazepam, mazapertine, olanzapine, oxazepam, pimozide, pipamperone, piracetam, promazine, risperidone, selfotel, seroquel, sulpiride, temazepam, thiothixene, triazolam, trifluperidol, ziprasidone); anti-stroke agents (lubeluzole, lubeluzole oxide, riluzole, aptiganel, eliprodil, remacemide); anti-migraine drugs (alniditan, sumatriptan); beta-adrenoceptor blocking agents (atenolol, carvedilol, metoprolol, nebivolol, propanolol); cardiac inotropic agents (digitoxin, digoxin, milrinone); corticosteroids (beclomethasone dipropionate, betamethasone, dexamethasone, hydrocortisone, methylprednisolone, prednisolone, prednisone, triamcinolone); disinfectants (chlorhexidine); diuretics (acetazolamide, frusemide, hydrochlorothiazide, isosorbide); anti-Parkinsonian drugs (bromocryptine mesylate, levodopa, selegiline HCl); enzymes; essential oils (anethole, anise oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol, thyme); gastro-intestinal agents (cimetidine, cisapride, clebopride, diphenoxylate HCl, domperidone, famotidine, lansoprazole, loperamide HCl, loperamide oxide, mesalazine, metoclopramide HCl mosapride, olsalazine, omeprazole, ranitidine, rabeprazole, ridogrel, sulphasalazine); haemostatics (aminocaproic acid); lipid regulating agents (lovastatin, pravastatin, probucol, simvastatin); local anaesthetics (benzocaine, lignocaine); opioid analgesics (buprenorphine HCl, codeine, dextromoramide, dihydrocodeine); parasympathomimetics (galanthamine, neostigmine, physostymine, tacrine, donepezil, ENA 713 (exelon), xanomeline); vasodilators (amlodipine, buflomedil, amyl nitrite, diltiazem, dipyridamole, glyceryl trinitrate, isosorbide dinitrate, lidoflazine, molsidomine, nicardipine, nifedipine, oxpentifylline, pentaerythritol tetranitrate).

The compositions according to the present invention are best presented as dosage forms suitable for oral, nasal, rectal or vaginal administration. To that purpose they are shaped as a tablet, preferably with a surface area sufficient to ensure effective bioadhesion to mucosa. Flat, disc shaped tablets are particularly preferred.

For oral applications, several buccal tablets have been developed. In imitation of the miconazole tablet described in Eur. J. Clin. Pharmacol. (1992) 43: 137–140, a similar miconazole tablet using sodium stearyl fumarate was prepared, but—as described below—now on an industrial scale. Said tablet comprises by weight based on the total weight of the tablet:

10% microfine miconazole nitrate;

82.8% drum dried waxy maize starch;

2% sodium stearyl fumarate;

5% carbomer 974 P; and 0.2% colloidal anhydrous silica.

In addition two tablets comprising respectively 1% and 5% of the active ingredient miconazole nitrate, and 91.8% and 87.8% drum dried waxy maize starch were prepared as well.

A buccal tablet comprising the triamcinolone (in imitation of Teijin's Aftach®) was also prepared. This tablet comprises by weight based on the total weight of the tablet 1% microfine triamcinolone;

91.8% drum dried waxy maize starch;

2% sodium stearyl fumarate;

5% carbomer 974 P; and 0.2% colloidal anhydrous silica.

The compositions according to the present invention can be prepared on a small scale by a wet-granulation process comprising the steps of intimately mixing the active ingredient, the pre-gelatinized starch, and optionally the hydrophilic matrix forming polymer, until homogenous in a suitable mixer, wetting the thus obtained mixture with a pharmaceutically acceptable non-aqueous solvent, pressing the wet mixture through a sieve having a maze width ranging from 1% to 1.8 mm;

drying the granulate; and mixing the dried granulate with sodium stearyl fumarate and optionally the glidant.

In order to prepare tablets, the process is followed by the further step of compressing the granulate with lubricant and optional glidant, into tablets.

However, this process is not amenable to large-scale production because of the disintegration of the granulate during the drying process in e.g. a fluid bed drier. Tablets can be prepared, however, by a dry process comprising the steps of:

intimately mixing the active ingredient, the pre-gelatinized starch and the hydrophilic matrix forming polymer in the dry state;

compacting the thus obtained mixture into a sheet;

breaking the sheet into a granules;

sieving the granules;

blending the granulate with the lubricant and optionally the glidant; and compressing the blend into tablets.

In this process, the blending steps can conveniently be conducted in art-known planetary mixers. Similarly, the dry compaction is conveniently conducted in art-known compaction machines at a force in the range of 4 to 15 kN, preferably in the range of 6 to 8 kN. The final compression step can be conducted at pressures ranging from 1500 to 3000 $kg.cm^{-2}$, in particular in the range of 1600 to 2000 $kg.cm^{-2}$.

The present invention is meant to extend to and include the products obtainable by the foregoing process.

The present invention also concerns the use of 0.2% to 5% (w/w) sodium stearyl fumarate as a lubricant and 80% to 98.8% (w/w) pre-gelatinized starch, 1 to 10% hydrophilic matrix forming polymer for the manufacture of a bioadhesive dosage form.

The buccal tablets according to the present invention can be administered as follows. A tablet is placed on the gingiva, preferably in the region of the upper canines, and is fixed by gently pressing on the cheek for 1 minute. The tablet then is preferably moistened with the tongue to prevent sticking of the tablet to the cheek.

The gingiva seem to be the best site or application because of the long-adhesion time (about 9 hours) and the slow clearance rate from the oral cavity.

Experimental Part

EXAMPLE 1
Miconazole Nitrate 10 mg Extended Release Buccal Tablet
Prior art formula (Eur. J. Clin. Pharmacol. (1992) 43: 137–140)

| | |
|---|---:|
| miconazole nitrate | 10 mg |
| drum-dried waxy maize | 82.8 mg |
| Carbopol 934 | 5 mg |
| silicon dioxide | 0.2 mg |
| sodium benzoate | 2 mg |

The powders were blended for 10 min in a Turbula mixer and were directly compressed into tablets having a total weight of 100 mg.

| Improved formula | |
|---|---:|
| miconazole nitrate (microfine) | 10 mg |
| drum-dried waxy maize | 82.8 mg |
| Carbopol 974 P | 5 mg |
| colloidal anhydrous silica | 0.2 mg |
| sodium stearyl fumarate | 2 mg |
| ethyl alcohol* | q.s. |

*ethyl alcohol is only used in the wet-granulation process of preparing tablets and does not appear in the end-product (approximately 0.1 g ethanol is used for every gram of the dry end formulation).

Wet-Granulation Process (Small Scale)

Miconazole nitrate, drum-dried waxy maize and Carbopol 974 P were mixed in a planetary mixer until homogenous and then wetted with ethyl alcohol. The dough-like paste was passed through a sieve (mesh openings of 1.8 mm) and allowed to dry at ambient temperature and pressure. When dried, the granulate was mixed with the colloidal anhydrous silica and the lubricant until homogenous. The granulate was then compressed into tablets having a total weight of 100 mg on a Korsch compression machine equipped with 6.5 mm flat punches.

Dry Compaction (Industrial Scale)

One kg of miconazole nitrate (microfine), 8.28 kg of drum dried waxy maize and 0.5 kg of polycarbophil (Carbopol 974P) were blended until homogenous in a planetary mixer. The blend was transferred to a roller compaction machine and compacted into sheets. The resulting sheets were broken and calibrated on an oscillating sieve (mesh openings of 1 mm). The thus obtained granules were then collected and mixed with 20 grams of colloidal anhydrous silica (Aerosil 200) and 200 grams of sodium stearyl fumarate until homogenous. The mixture was compressed into 100,000 flat tablets having a nominal weight of 100 mg on a Korsch compression machine equipped with 6.5 mm flat punches.

EXAMPLE 2

Following the wet granulation process of example 1, two other miconazole nitrate extended release buccal tablets with the formulations given below were prepared

| | 1 mg tablet | 5 mg tablet |
|---|---:|---:|
| miconazole nitrate (microfine) | 1 mg | 5 mg |
| drum dried waxy maize starch | 91.8 mg | 87.8 mg |
| Carbopol 974 P | 5 mg | 5 mg |
| colloidal anhydrous silica | 0.2 mg | 0.2 mg |
| sodium stearyl fumarate | 2 mg | 2 mg |
| ethyl alcohol* | q.s. | q.s. |

*ethanol does not appear in the end product (approximately 0.1 g ethanol is used for every gram of the dry end formulation)

EXAMPLE 3
Triamcinolone 1 mg Extended Release Buccal Tablet

| | |
|---|---:|
| microfine triamcinolone | 1 mg |
| drum dried waxy maize starch | 91.8 mg |
| sodium stearyl fumarate | 2 mg |
| carbomer 974 P | 5 mg |
| colloidal anhydrous silica | 0.2 mg |

Following the small scale wet granulation method and the industrial dry compaction method described in the previous example, batches of triamcinolone 1 mg extended release buccal tablets were prepared.

EXAMPLE 4
Miconazole Concentration in Saliva from Healthy Volunteers After Single and Repeated Oral Administration ($\mu$l/ml)

| Treatment | day | time | median | mean | S.D. | n |
|---|---|---|---:|---:|---:|---:|
| A | 1 | 0 h | NQ | NQ | — | 12 |
| | | 15 min | 2.5 | 5.6 | 7.5 | 12 |
| | | 30 min | 3.6 | 14.2 | 25.5 | 12 |
| | | 45 min | 20.5 | 20.8 | 20.8 | 12 |
| | | 60 min | 12.1 | 18.7 | 28.6 | 12 |
| | | 90 min | 22.4 | 28.1 | 25.5 | 12 |
| | | 2 h | 21.8 | 24.0 | 15.1 | 12 |
| | | 3 h | 33.9 | 35.3 | 20.5 | 12 |
| | | 4 h | 37.8 | 36.3 | 16.9 | 12 |
| | | 6 h | 24.7 | 25.3 | 16.0 | 12 |
| | | 8 h | 7.3 | 14.7 | 16.3 | 12 |
| | | 12 h | NQ | NQ | — | 12 |
| | 8 | 0 h | NQ | NQ | — | 12 |
| | | 15 min | NQ | 4.2 | 6.7 | 12 |
| | | 30 min | 4.7 | 16.6 | 34.7 | 12 |
| | | 45 min | 7.2 | 20.4 | 32.9 | 12 |
| | | 60 min | 8.0 | 24.5 | 32.8 | 12 |
| | | 90 min | 13.8 | 31.2 | 34.2 | 12 |
| | | 2 h | 23.0 | 29.7 | 18.7 | 12 |
| | | 3 h | 33.9 | 35.7 | 19.5 | 12 |
| | | 4 h | 17.8 | 24.3 | 18.1 | 12 |
| | | 6 h | 14.0 | 15.9 | 16.6 | 12 |
| | | 8 h | 13.1 | 16.9 | 18.4 | 12 |
| | | 12 h | NQ | NQ | — | 12 |
| B | 1 | 0 h | NQ | NQ | — | 12 |
| | | 5 min | 41.3 | 60.2 | 53.2 | 12 |
| | | 15 min | 6.2 | 8.3 | 9.8 | 12 |
| | | 30 min | 1.5 | 1.9 | 1.8 | 12 |
| | | 45 min | NQ | NQ | — | 12 |
| | | 60 min | NQ | NQ | — | 12 |
| | | 90 min | NQ | NQ | — | 12 |
| | | 2 h | NQ | NQ | — | 12 |
| | | 3 h | NQ | NQ | — | 12 |
| | | 4 h | NQ | NQ | — | 12 |
| | 8 | 0 h | NQ | NQ | — | 12 |
| | | 5 min | 56.9 | 75.9 | 64.6 | 12 |
| | | 15 min | 3.2 | 5.3 | 4.4 | 12 |
| | | 30 min | 1.1 | 1.7 | 2.3 | 12 |
| | | 45 min | NQ | NQ | — | 12 |
| | | 60 min | NQ | NQ | — | 12 |

-continued

| Treatment | day | time | median | mean | S.D. | n |
|---|---|---|---|---|---|---|
| | | 90 min | NQ | NQ | — | 12 |
| | | 2 h | NQ | NQ | — | 12 |
| | | 3 h | NQ | NQ | — | 12 |
| | | 4 h | NQ | NQ | — | 12 |

Treatment A: 10 mg miconazole nitrate (improved formula of Example 1 prepared by the wet granulation process) as a bioadhesive buccal tablet o.d. for eight days.
Treatment B: 60 mg miconazole as 3 grams of an oral get (20 mg/g) q.i.d. for eight days
NQ: not quantifiable by the GC-method (<1.0 µg/ml)

EXAMPLE 5

In vitro dissolution studies were performed on the improved tablet formulations of example 1. The medium was 600 ml of a mixture of 2-propanol/water (60/40) at 37° C. in Apparatus 2 (USP 23, <711> Dissolution, pp. 1791–1793) (paddle, 50 rpm). In each dissolution test three tablets of 10 mg (giving a total dosis of 30 mg) miconazole nitrate were used; at regular intervals a sample of 3 ml was withdrawn from the dissolution medium and the concentration of miconazole dissolved therein was determined by measuring the absorbance at UV wavelengths-range: 260–300 mm. In the following tables, amount of miconazole dissolved in the medium is expressed as (% w/w) of the total dose.

A. Tablets prepared by the wet-granulation process.

Calculated concentration (% w/w) of the active dose

| Time (min) | sample 1 | sample 2 | sample 3 | sample 4 | sample 5 | sample 6 | average |
|---|---|---|---|---|---|---|---|
| 0 | 0.00 | 0.00 | 0.00 | 0.00 | 0.00 | 0.00 | 0.00 |
| 15 | 8.26 | 8.98 | 9.87 | 8.89 | 9.87 | 12.57 | 9.74 |
| 30 | 16.16 | 14.36 | 16.16 | 13.46 | 15.26 | 15.26 | 15.11 |
| 60 | 21.54 | 20.64 | 22.44 | 21.54 | 20.64 | 21.54 | 21.39 |
| 120 | 31.41 | 31.41 | 35.90 | 34.11 | 32.31 | 32.31 | 32.91 |
| 180 | 37.70 | 39.49 | 38.59 | 38.59 | 40.39 | 39.49 | 39.04 |
| 240 | 49.37 | 51.16 | 50.26 | 48.47 | 50.26 | 49.37 | 49.81 |
| 360 | 55.65 | 58.34 | 60.14 | 58.34 | 58.34 | 60.14 | 58.49 |
| 480 | 64.62 | 66.42 | 68.21 | 66.42 | 67.32 | 65.52 | 66.42 |
| 1440 | 95.14 | 95.14 | 98.73 | 98.73 | 97.83 | 96.04 | 96.94 |

B. Tablets prepared by the dry-compaction process

Calculated concentration (% w/w) of the active dose

| Time (min) | sample 1 | sample 2 | sample 3 | sample 4 | sample 5 | sample 6 | average |
|---|---|---|---|---|---|---|---|
| 0 | 0.00 | 0.00 | 0.00 | 0.00 | 0.00 | 0.00 | 0.00 |
| 30 | 18.85 | 18.85 | 17.95 | 15.26 | 21.54 | 18.76 | 18.53 |
| 60 | 43.08 | 33.21 | 35.00 | 32.31 | 39.49 | 35.90 | 36.50 |
| 90 | 58.34 | 53.85 | 52.06 | 51.16 | 54.75 | 50.26 | 53.40 |
| 180 | 83.47 | 75.39 | 80.78 | 83.47 | 78.09 | 76.29 | 79.58 |
| 240 | 100.53 | 85.27 | 85 27 | 96.94 | 86.16 | 82.57 | 89.46 |

It should be noted that the above dissolution data were obtained in the unusual medium of 2-propanol/water (60/40) in order to accelerate the dissolution rate. Also, varying the compression pressure and compaction forces, yielded tablets having both slower and faster dissolution rates than these shown in the tables above. In short, the above data are provided for the purpose of showing the extended release properties of the tablets prepared according to the present invention, but—in and of themselves—may not be taken to show any definite characteristics discernable between the wet granuation process and the dry compaction process.

EXAMPLE 6
In Vitro Determination of Bioadhesion

The bioadhesion of the tablets was evaluated according to a previously described method (S. Bouckaert, J. P. Remon,. In vitro bioadhesion of a buccal miconazole slow-release tablet. J. Pharm. Pharmacol. 45: 504–507 (1993). The detachment force and the work of adhesion were determined as the height and the area under the curve of the force vs extension diagram. The apparatus consisted of a tensile testing machine (type L1000R, Lloyd Instruments, Segenworth, Fareham, UK), equipped with a 20 N load cell. Porcine gingiva were obtained from a slaughter house where they were excised directly after slaughtering. The mucosa ($\pm 100$ mm$^2$) were stored at $-20°$ C. in isotonic buffered saline pH 7.4 (2.38 g $Na_2HPO_4H_2O$, 19 g $KH_2PO_4$, 8.0 g NaCl made up to 1000 ml with demineralised water).

The porcine gingival tissue was attached with cyanoacrylate glue (Loctite, Belgium) to a lower Teflon support, while the tablet was attached to an upper aluminium punch. After hydrating the mucosa with 15 µl of the isotonic phosphate buffered saline, the tablet was fixed on the mucosa applying a force of 0.5 N for 5 min. After the initial contact, the beaker was filled with 125 ml isotonic buffered saline pH 7.4. Next, the tablet and mucosa were pulled apart at a speed of 5 mm.min$^{-1}$ until a complete rupture of the tablet-mucosa bond was obtained.

The results are reported as individual and average values ($\pm$SD) in the following tables.

|   | Sample 1 | sample 2 | sample 3 | sample 4 | sample 5 | average | SD |
|---|---|---|---|---|---|---|---|
| Detachment Force (N) ||||||||
| A | 1.219 | 1.086 | 1.068 | 1.353 | 1.126 | 1.1704 | 0.1176 |
| B | 1.285 | 1.466 | 1.581 | 1.373 | 1.524 | 1.4458 | 0.1183 |
| C | 2.08 | 2.684 | 2.998 | 3.068 | 2.265 | 2.619 | 0.437 |
| Work of adhesion (mJ) ||||||||
| A | 0.092 | 0.115 | 0.131 | 0.208 | 0.122 | 0.1336 | 0.044 |
| B | 0.263 | 0.142 | 0.116 | 0.102 | 0.158 | 0.1562 | 0.0636 |
| C | 0.570 | 0.662 | 0.658 | 0.634 | 0.498 | 0.604 | 0.070 |

A: 10 mg miconazole tablet (improved formula of Example 1, prepared by the wet granulation process).
B: 10 mg miconazole tablet (improved formula of Example 1, prepared by the dry compaction process).
C: 1 mg triamcinolone tablet of Example 3, prepared by the wet granulation process.

I claim:

1. A bioadhesive pharmaceutical composition comprising a pharmaceutically effective amount of an active ingredient, from 80% to 98.8% w/w pre-gelatinized starch, and from 1% to 10% w/w of a hydrophilic matrix forming polymer, characterized in that the composition further comprises from 0.2% to 5% w/w alkali $C_{16-22}$alkyl fumarate as a lubricant.

2. A composition according to claim 1 wherein the lubricant is micronized sodium stearyl fumarate.

3. A composition according to claim 1 comprising from 2.5 to 7.5% w/w of a hydrophilic matrix forming polymer.

4. A composition according to claim 3 wherein the polymer is selected from the group consisting of polyacrylic acid, carbomer, hydroxyethyl cellulose, hydroxypropyl cellulose, hydroxypropyl methylcellulose, sodium carboxymethylcellulose, polyvinyl alcohol and a mixture thereof.

5. A composition according to claim 1 further comprising a glidant.

6. A composition according to claim 5 wherein the glidant is colloidal anhydrous silica.

7. A composition according to claim 1 comprising by weight based on the total weight
   from 0.001% to 10% active ingredient;
   from 80% to 98.8% pre-gelatinized starch;
   from 1% to 10% hydrophilic matrix forming polymer;
   from 0.2% to 5% sodium stearyl fumarate; and
   from 0% to 1% glidant.

8. A dosage form suitable for buccal, nasal, rectal or vaginal administration which comprises a composition as claimed in claim 1 and which is shaped as a tablet.

9. A buccal tablet according to claim 8 comprising by weight based on the total weight of the tablet
   10% microfine miconazole nitrate;
   82.8% drum dried waxy maize starch;
   2% sodium stearyl fumarate;
   5% polyacrylic acid polymer; and
   0.2% colloidal anhydrous silica.

10. A buccal tablet according to claim 8 comprising by weight based on the total weight of the tablet
    1% microfine triamcinolone;
    91.8% drum dried waxy maize starch;
    2% sodium stearyl fumarate;
    5% polyacrylic acid polymer; and
    0.2% colloidal anhydrous silica.

11. A dry process for preparing tablets according to claim 1 comprising the steps of:
    mixing the pharmaceutically active ingredient, the pre-gelatinized starch and the hydrophilic matrix forming polymer in the dry state until homogenous;
    compacting the thus obtained mixture into a sheet;
    breaking the sheet into a granulate;
    blending the granulate with the lubricant and optionally a glidant; and
    compressing the blend into tablets.

12. A tablet made by the process according to claim 11.

* * * * *